United States Patent
Fetzer et al.

(10) Patent No.: US 10,119,939 B2
(45) Date of Patent: Nov. 6, 2018

(54) VEHICLE AXLE INSPECTION SYSTEMS AND METHODS

(71) Applicant: The Boeing Company, Chicago, IL (US)

(72) Inventors: Barry A. Fetzer, Renton, WA (US); Gary E. Georgeson, Tacoma, WA (US); Morteza Safai, Newcastle, WA (US); Jeffrey G. Thompson, Auburn, WA (US); Steven Kenneth Brady, Renton, WA (US); John R. Hull, Sammamish, WA (US)

(73) Assignee: The Boeing Company, Chicago, IL (US)

( * ) Notice: Subject to any disclaimer, the term of this patent is extended or adjusted under 35 U.S.C. 154(b) by 268 days.

(21) Appl. No.: 15/159,979

(22) Filed: May 20, 2016

(65) Prior Publication Data
US 2017/0336367 A1    Nov. 23, 2017

(51) Int. Cl.
| G01N 29/22 | (2006.01) |
| G01N 29/27 | (2006.01) |
| G01N 29/44 | (2006.01) |
| G01N 29/04 | (2006.01) |
| G01N 29/275 | (2006.01) |

(52) U.S. Cl.
CPC ......... *G01N 29/043* (2013.01); *G01N 29/225* (2013.01); *G01N 29/27* (2013.01); *G01N 29/275* (2013.01); *G01N 29/4427* (2013.01); *G01N 2291/044* (2013.01); *G01N 2291/2626* (2013.01); *G01N 2291/2634* (2013.01)

(58) Field of Classification Search
CPC .. G01N 29/043; G01N 29/225; G01N 29/275; G01N 29/4427; G01N 29/27; G01N 2291/044; G01N 2291/2634; G01N 2291/2626
USPC .......................................................... 73/636
See application file for complete search history.

(56) References Cited

U.S. PATENT DOCUMENTS

| 3,812,708 | A | * | 5/1974 | Cowan | G01B 17/06 73/597 |
| 3,978,712 | A | * | 9/1976 | Cowan | G01B 17/06 73/597 |
| 4,402,374 | A | * | 9/1983 | Knur | B60K 7/0007 180/65.7 |
| 5,864,065 | A | * | 1/1999 | Prorok | G01N 29/07 73/598 |
| 6,832,513 | B2 | * | 12/2004 | Weiss | G01M 17/02 73/146 |

(Continued)

FOREIGN PATENT DOCUMENTS

RU        2138403        *   9/1999

*Primary Examiner* — J M Saint Surin
(74) *Attorney, Agent, or Firm* — Joseph M. Butscher; The Small Patent Law Group, LLC

(57) ABSTRACT

A vehicle examination system includes an axle inspection system that is configured to inspect an axle of a vehicle. The axle inspection system includes an ultrasound scanning assembly, and an axle coupler that retains the ultrasound scanning assembly. The axle coupler is configured to moveably secure the ultrasound scanning assembly to the axle. An axle inspection control unit is in communication with the ultrasound scanning assembly. The axle inspection control unit is configured to control the ultrasound scanning assembly to ultrasonically scan the axle for anomalies as the vehicle moves.

23 Claims, 8 Drawing Sheets

(56) References Cited

U.S. PATENT DOCUMENTS

| | | | | |
|---|---|---|---|---|
| 7,555,954 B2* | 7/2009 | Pagano | ............... | G01N 29/043 |
| | | | | 73/620 |
| 8,181,529 B2* | 5/2012 | Crocker | ................ | B61K 9/10 |
| | | | | 73/636 |
| 8,596,125 B2* | 12/2013 | Oliver | ................ | G01M 17/10 |
| | | | | 73/620 |
| 8,596,126 B2* | 12/2013 | Oliver | ................ | B61K 9/12 |
| | | | | 73/620 |
| 9,027,405 B2* | 5/2015 | Desai | ................ | G01N 29/0645 |
| | | | | 73/622 |
| 2002/0070100 A1* | 6/2002 | Kalm | ................ | B65G 13/11 |
| | | | | 198/781.01 |
| 2015/0068312 A1* | 3/2015 | Jenkins | ................ | G01N 29/262 |
| | | | | 73/638 |

* cited by examiner

VEHICLE AXLE INSPECTION SYSTEMS AND METHODS

FIELD OF THE DISCLOSURE

Embodiments of the present disclosure generally relate to systems, methods, and assemblies for inspecting axles of vehicles, such as axles of train cars.

BACKGROUND OF THE DISCLOSURE

Various vehicles include wheels connected together by axles. For example, train cars include axles that connect wheels that are supported on rails. Each axle connects to two wheels at or proximate to opposite ends of the axle.

During operation of a train, anomalies may form on or within the axles. As can be appreciated, normal wear and tear of the axles over an operational lifetime may cause various anomalies, such as cracks, strains, stresses, cavities, corrosion, and/or the like to form on or within the axles.

In general, axles of train cars are manually inspected. An individual maneuvers underneath the train car to manually inspect each axle when the train car is parked or otherwise stopped at a location on the tracks. As another example, the axles may be removed from the train cars for inspection.

Accordingly, in order to inspect axles of train cars, the train car is first stopped and maintained in a stationary position. An individual then manually inspects each axle, either by maneuvering underneath the train car, or after each axle has been removed from the train car. In short, the process of inspecting axles of train cars is time and labor intensive. Further, the process of inspecting a large number of axles of a long train may prove to be an overwhelming task. An individual inspecting the axles may become fatigued and also be susceptible to repetitive stress injuries as a consequence of manipulating an inspection device at ergonomically inefficient positions. Moreover, the train car being inspected, which is stopped on the tracks, prevents other rail cars from moving over that portion of the tracks until after the inspection process is complete.

SUMMARY OF THE DISCLOSURE

A need exists for a system and method of efficiently inspecting axles of vehicles. A need exists for a system and method of automatically inspecting axles of vehicles. A need exists for a system and method of inspecting axles of vehicles as the vehicles move (to prevent, minimize, or otherwise reduce track or route bottlenecks, for example).

With those needs in mind, certain embodiments of the present disclosure provide a vehicle examination system that includes an axle inspection system that is configured to inspect an axle of a vehicle. The axle inspection system includes an ultrasound scanning assembly, and an axle coupler that retains the ultrasound scanning assembly. The axle coupler is configured to moveably secure the ultrasound scanning assembly to the axle.

An axle inspection control unit may be in communication with the ultrasound scanning assembly. The axle inspection control unit is configured to control the ultrasound scanning assembly to ultrasonically scan the axle for anomalies as the vehicle moves.

In at least one embodiment, the axle coupler axially moves over the axle as the axle rotates. The axle coupler may be configured to be coupled to the axle as the vehicle is moving.

The axle inspection system may include a memory coupled to the axle inspection control unit. The memory may store historical data regarding anomalies in axles. The axle inspection control unit may control the ultrasound scanning assembly to transmit ultrasound signals into areas of the axle based on the historical data.

The axle inspection system may include an actuator that propels the axle coupler over the axle. In at least one embodiment, rotation of the axle causes the actuator to propel the axle coupler over the axle. In at least one embodiment, the actuator includes a motor that propels the axle coupler over the axle.

In at least one embodiment, the ultrasound scanning assembly includes at least ultrasound probe. The ultrasound probe(s) may be configured to radially scan the axle. Additionally, or alternatively, the ultrasound probe(s) may be configured to axially scan the axle.

The axle coupler may include at least one bracket that is configured to directly engage the axle. The bracket(s) may include a plurality of spring-biased rollers that are configured to engage an outer surface of the bracket. The bracket(s) may include a C-shaped bracket. The C-shaped bracket may include an open upper end. The axle coupler may be configured to be urged upwardly onto the axle.

In at least one embodiment, the bracket(s) includes an upper bracket pivotally connected to a lower bracket. The upper and lower brackets are configured to close around an outer circumference of the axle.

The axle inspection system may include at least one brush inwardly extending from the axle coupler. The brush is configured to wipe an outer surface of the axle as the axle rotates.

The axle inspection system may include at least one proximity sensor that is configured to sense a distance between the axle inspection system and at least one wheel connected to the axle.

The axle inspection system may include a connecting link that connects the axle coupler to another axle coupler that retains another ultrasound scanning assembly.

The vehicle examination system may include a staging system including an internal chamber that houses a couplant reservoir, a data storage unit, and a power recharger. The axle inspection system may be configured to be moved between the staging system and the axle.

The vehicle examination system may include an installation system including an installation cart that is configured to move along with the vehicle and install the axle inspection system on the axle of the vehicle as the vehicle and the installation cart move. The installation cart may include an installation device that is configured to automatically install the axle inspection system onto the axle.

The vehicle examination system may include an imaging device that is configured to procure an image of the axle. The image is analyzed to determine if the axle inspection system is compatible with the axle.

Certain embodiments of the present disclosure provide a vehicle examination method that includes inspecting an axle of a vehicle with an axle inspection system. The inspecting comprises retaining an ultrasound scanning assembly with an axle coupler, moveably securing the ultrasound scanning assembly to the axle with the axle coupler, communicatively coupling an axle inspection control unit to the ultrasound scanning assembly, moving the vehicle, and controlling the ultrasound scanning assembly with the axle inspection control unit to ultrasonically scan the axle for anomalies during the moving.

DETAILED DESCRIPTION OF THE DISCLOSURE

Figure 1:
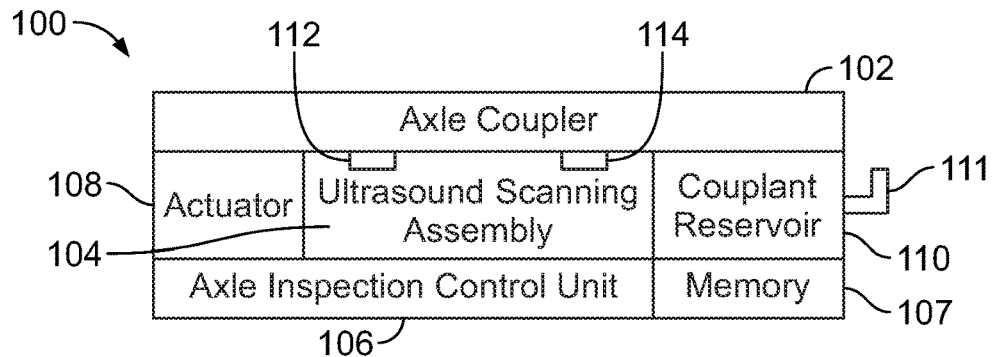
FIG. 1 illustrates a schematic block diagram of an axle inspection system, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition may include additional elements not having that condition.

Embodiments of the present disclosure provide an axle inspection system and method that are configured to automatically inspect vehicle axles (such as those or rail or train cars) as the vehicle moves along a route, such as along railroad tracks. The axle inspection system includes an ultrasound scanning assembly that includes one or more ultrasound transducer arrays that are configured to transmit ultrasonic signals into an axle of a vehicle. The ultrasonic signals reflect off anomalies on and/or within the axle and received by the ultrasound transducer array(s). An axle inspection control unit analyzes the transmitted and reflected ultrasonic signals to determine the existence and location of any anomalies within the axle.

The axle inspection system and method are configured to inspect an axle as it rotates, such as when the vehicle is moving. As such, embodiments of the present disclosure provide axle inspection systems and methods that do not require the axle to be removed or the vehicle to be stopped in order for inspection to occur. Certain embodiments of the present disclosure provide an axle inspection system that is attached to an axle while the vehicle is moving. In at least one other embodiment, the axle inspection system is manually secured to the axle before the vehicle moves.

The anomalies on and/or within an axle of the vehicle include features that may form over time from normal wear and tear of the axle during operation of the vehicle. For example, the anomalies includes imperfections, defects, irregularities and the like such as voids, cavities, stresses, strains, cracks, corrosion, and/or the like that may form on and/or within the axle over time.

Certain embodiments of the present disclosure provide axle inspection systems and methods that allow for axle inspection without the need to remove the axle. Further, embodiments of the present disclosure eliminate, minimize, or otherwise reduce the amount of time individuals are underneath a vehicle (such as relative to prior inspection methods in which individuals maneuvered underneath train cars and individually manually inspected each axle). The axle inspection systems include one or more phased array ultrasonic transducers that are configured to steer ultrasonic signals towards and into portions of an axle in which anomalies typically arise. For example, the ultrasonic transducer(s) may be configured to emit ultrasonic signals to areas of the axle based on historical data regarding locations where anomalies frequently arise. In at least one embodiment, the axle inspection system includes a self-propelled axle coupler (such as a yoke, collar, bracket, and/or the like). Multiple axle couplers may be used to couple an axle inspection system to multiple axles at the same time.

Certain embodiments of the present disclosure provide an axle inspection system that is configured to inspect one or more axles of a vehicle. The vehicle may include a frame and at least one axle coupled to the frame. In at least one embodiment, the axle inspection system includes an axle coupler, which may be or otherwise include a probe carrier, that is configured to be installed on the axle, an ultrasound probe that is configured to be coupled to the axle coupler and acquire ultrasound information of the axle, and a drive system operable to move the ultrasound probe along a length of the axle while the probe is acquiring the ultrasound information.

The drive system may include a linear actuator that is configured to move the ultrasound probe along a length of the axle. In at least one embodiment, the drive system may include a worm gear, wheel, gear(s), pulley(s), and/or the like coupled to the axle coupler.

The axle coupler may include a plurality of bearings that are configured to moveably couple the axle coupler to the axle. A second axle coupler may be installed on a second axle.

In at least one embodiment, the axle coupler includes a pressure sensor that is configured to output a signal when the probe carrier contacts an end of the axle. The axle coupler may include a hinged link arm that allows for the axle coupler to be removably secured to an axle.

In at least one embodiment, an installation cart is configured to move alongside or underneath a vehicle. The installation car includes a device installation and removal apparatus that is configured to allow the axle coupler to be installed on the vehicle.

FIG. 1 illustrates a schematic block diagram of an axle inspection system 100, according to an embodiment of the present disclosure. The axle inspection system 100 includes an axle coupler 102, an ultrasound scanning assembly 104, and an axle inspection control unit 106, such as may include or otherwise be in communication with a memory 107. In at least one embodiment, the axle inspection 100 also includes an actuator 108, a couplant reservoir 110, and a couplant emitter 111.

The axle coupler 102 may be or include a yoke, bracket, collar, or the like that is configured to removably secure the ultrasound scanning assembly 104 to one or more axles of a vehicle, such as a train car. The axle coupler 102 carries or otherwise retains the ultrasound scanning assembly 104, and may be referred to as a probe carrier. In at least one embodiment, the axle coupler 102 includes a C-shaped collar that is configured to be securely coupled to an axle (such as by clamping onto the axle). In at least one other embodiment, the axle coupler 102 includes a hinge collar that is configured to open and close around an outer circumference of an axle. In at least one other embodiment, the axle coupler 102 includes a sleeve that may be opened and slid over a portion of the axle. In at least one other embodiment, the axle coupler 102 includes a bracket that couples to the axle through magnetism, one or more fasteners, and/or the like.

The ultrasound scanning assembly 104 includes at least one ultrasound probe that is configured to transmit and receive ultrasonic signals with respect to an axle of a vehicle. For example, in at least one embodiment, the ultrasound scanning assembly 104 includes a first ultrasound probe 112 (such as a transducer array) and a second ultrasound probe 114 (such as another transducer array). The first ultrasound probe 112 includes a curved phased ultrasound transducer array that is configured to transmit and receive ultrasound signals radially with respect to the axle (that is, over radial directions with respect to the axle). The second ultrasound probe 114 includes a linear phased ultrasound transducer array that is configured to transmit and receive ultrasound signals axially with respect to the axle (that is, over directions along a length of the axle). Each of the first and second ultrasound probes 112 and 114 may include a pulse generator, such as a phased array transducer having a plurality of ultrasound elements. Optionally, each of the first and second ultrasound probes 112 and 114 may include a single element ultrasound transducer. Alternatively, the ultrasound scanning assembly 104 includes the first ultrasound probe 112, but not the second ultrasound probe 114.

In at least one other embodiment, the ultrasound scanning assembly 104 includes the second ultrasound probe 114, but not the first ultrasound probe 112. In at least one other embodiment, the ultrasound scanning assembly 104 includes a plurality of first ultrasound probes 112 and/or a plurality of second ultrasound probes 114. It is to be understood that the terms first and second are merely to enumerate the types of ultrasound transducer arrays. The first ultrasound transducer probe may be a second ultrasound probe, and vice versa.

The axle inspection control unit 106 is in communication with the ultrasound scanning assembly 104 through one or more wired or wireless connections. The axle inspection control unit 106 may be directly or indirectly coupled to the axle coupler 102, for example. In at least one embodiment, the axle inspection control unit 106 is secured within a housing that is mounted onto the axle coupler 102. In at least one other embodiment, the axle inspection control unit 106 is remotely located from the axle coupler 102. For example, the axle inspection control unit 106 and/or the memory 107 may be within a central monitoring station that is remotely located from the axle coupler 102 and the ultrasound scanning assembly 104.

The axle inspection control unit 106 is configured to control operation of the ultrasound scanning assembly 104. For example, the axle inspection control unit 106 operates the ultrasound scanning assembly to transmit and steer ultrasound signals into an axle. The transmitted ultrasound signals reflect off anomalies on and within the axle. The reflected ultrasound signals are received by the ultrasound scanning assembly 104 and analyzed by the axle inspection control unit 106 to determine the location and nature of the anomalies on and/or within the axle.

The axle inspection control unit 106 is coupled to the memory 107, which stores historical data regarding typical anomalies on or within an axle. In at least one embodiment, the axle inspection control unit 106 operates the ultrasound scanning assembly 104 to steer the transmitted ultrasound signals towards such areas based on the historical data stored in the memory 107.

The actuator 108 may be part of the axle coupler 102. The actuator 108 is configured to propel the axle coupler 102 (and therefore the ultrasound scanning assembly 104) over a length of the axle. The actuator 108 may include a motor, such as an electromechanical motor, that is configured to axially move the axle inspection system 100 over an axle. Optionally, the actuator 108 may include one or more a worm screw, wheel(s), track(s), gear(s), pulley(s), and/or the like that are configured to automatically move the axle inspection system 100 along the axle as the axle rotates. That is, in response to rotation of the axle, the actuator 108 propels the axle coupler 102 axially over the axle. Alternatively, the axle inspection system 100 may not include the actuator 108.

The couplant reservoir 110 includes a tank that is configured to store couplant, such as water, which is configured to efficiently couple the ultrasound scanning assembly 104 to the axle. The couplant emitter 111 may include one or more nozzle(s), hose(s), tube(s), and/or the like that are configured to spray or otherwise deposit the couplant between the ultrasound scanning assembly 104 and the axle. In at least one embodiment, the couplant is emitted between the axle and a flexible, acoustically transparent membrane. The axle inspection control unit 106 may be in communication with the couplant emitter 111 and configured to control the amount of couplant that is emitted onto the axle. Alternatively, the axle inspection system 100 may not include the couplant reservoir 110 or the couplant emitter 111.

Figure 2:
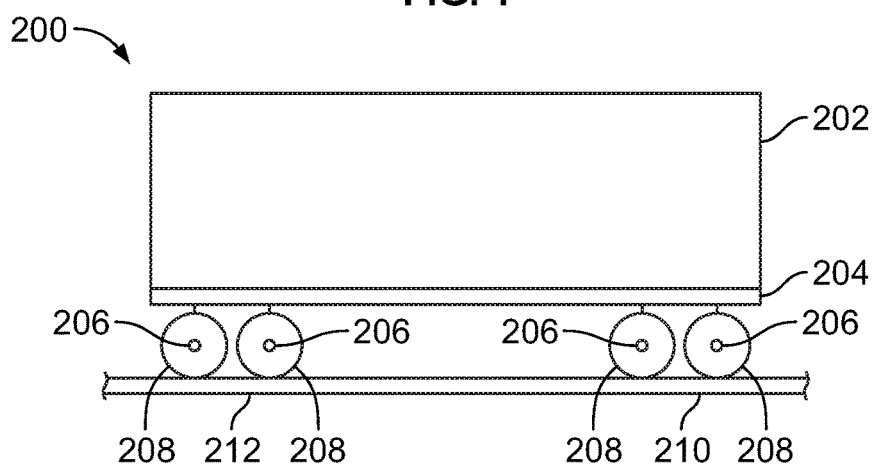
FIG. 2 illustrates a lateral view of a vehicle, according to an embodiment of the present disclosure.

FIG. 2 illustrates a lateral view of a vehicle 200, according to an embodiment of the present disclosure. The vehicle 200 may be a powered vehicle (such as including one or more engines), or an unpowered vehicle (such as a car that is configured to be directly or indirectly coupled to a powered vehicle). The vehicle 200 includes a main body 202 coupled to a frame 204. One or more axles 206 are moveably coupled to the frame 204. Wheels 208 are rotatably coupled to the axles 206. For example, a wheel 208 is rotatably coupled to or proximate to each end of an axle 206. In at least one embodiment, rotation of the wheels 208 causes a corresponding rotation of the axles 206.

The wheels 208 are configured to convey the vehicle 200 over a route 210, which may include one or more tracks. As shown in FIG. 1, the vehicle 200 is a train car that is supported on railroad tracks 212, which define the route 210. Alternatively, the vehicle 200 may be an automobile, a truck, trailer, cart, and/or the like that is not supported on rails.

Referring to FIGS. 1 and 2, in order to inspect the axles 206, the vehicle 200 may first be stopped. An individual may then securely mount the axle inspection system 100 to one or more of the axles 206. Optionally, an installation system may be used to securely mount the axle inspection system 100 to one or more of the axles 206 as the vehicle 200 is moving.

After the axle inspection system(s) 100 is secured to the axle(s) 206, the axle inspection control unit 106 activates the ultrasound scanning assembly 104 to transmit ultrasound signals into the axle(s) 206 as the vehicle 200 moves over the route 210. As such, the axles 206 rotate during operation of the axle inspection system(s) 100. Reflected ultrasound signals are received by the ultrasound scanning assembly 104, which then analyzes the transmitted and reflected ultrasound signals to determine the existence, nature, and location of anomalies on and within the axles 206. The axle inspection system 100 may store anomaly data (regarding detected anomalies) within the memory 107. A central monitoring station may be in communication with the axle inspection control unit 106 and receive the anomaly data therefrom, such as through one or more wired or wireless connections.

As each axle 206 rotates, the ultrasound scanning assembly 104 may remain radially fixed with respect to the axle 206. Rotation of the axle 206 relative to the ultrasound scanning assembly 104 ensures that the ultrasound scanning assembly 104 emits transmitted signals and receives reflected signals with respect to an entire circumference of the axle 206. The motion of the axle 206 ensures full inspection coverage thereof by the axle inspection system 100. For example, an entire circumferential outer surface of the axle 206 may be rotated in close proximity of the ultrasound scanning assembly 104. After the axle inspection is complete, the axle inspection system 100 is removed from the axle 206, at which time the axle inspection system 100 may be installed on a different axle 206. The process may be repeated until each of the respective axles 206 is inspected.

As used herein, the term "control unit," "unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms.

The axle inspection control unit 106, for example, is configured to execute a set of instructions that are stored in one or more storage elements (such as one or more memories), in order to process data. For example, the axle inspection control unit 106 may include or be coupled to one or more memories (such as the memory 107). The storage elements may also store data or other information as desired or needed. The storage elements may be in the form of an information source or a physical memory element within a processing machine.

The set of instructions may include various commands that instruct the axle inspection control unit 106 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software may also include modular programming in the form of object-oriented programming. The processing of input data by the processing machine may be in response to user commands, in response to results of previous processing, or in response to a request made by another processing machine.

The diagrams of embodiments herein may illustrate one or more control or processing units, such as the axle inspection control unit 106. It is to be understood that the processing or control units may represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control units may represent processing circuitry such as one or more of a field programmable gate array (FPGA), application specific integrated circuit (ASIC), microprocessor(s), a quantum computing device, and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 3:
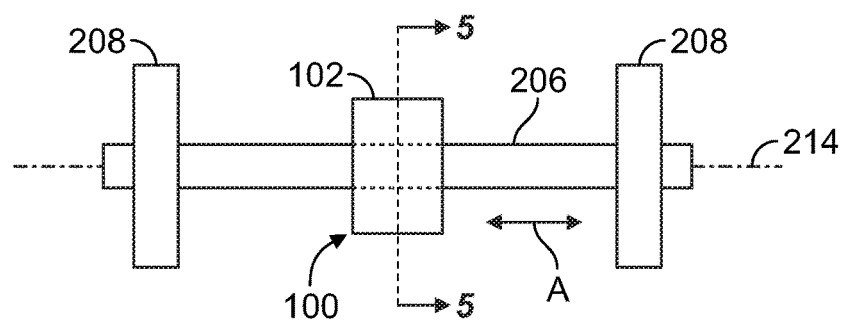
FIG. 3 illustrates a top view of an axle inspection system coupled to an axle, according to an embodiment of the present disclosure.

FIG. 3 illustrates a top view of the axle inspection system 100 coupled to an axle 206, according to an embodiment of the present disclosure. As shown, the axle coupler 102 removably secures the axle inspection system 100 around at least a portion of the axle 206. Referring to FIGS. 1-3, as the axle 206 rotates about a longitudinal axis 214, the axle inspection system 100 moves axially over the axle 206 in the directions of arrow A. In at least one embodiment, the rotational movement of the axle 206 drives the motion of the axle inspection system 100. For example, the actuator 108 may include a worm wheel that is operatively coupled to the axle 206. The rotational motion of the axle 206 drives the linear motion of the axle inspection system 100 over the axle 206. In at least one other embodiment, the actuator 108 may be or include a motor that drives the axle inspection system 100 over the axle 206 in the directions of arrow A.

As the axle inspection system 100 moves over the axle 206 in the directions of arrow A, the ultrasound scanning assembly 104 gathers anomaly data of the axle 206, which may be analyzed by the axle inspection control unit 106 and/or stored in the memory 107 to provide information about the existence, nature, and location of anomalies on and within the axle 206. The axle inspection system 100 may extend over a greater or lesser length of the axle 206 than shown.

Figure 4:
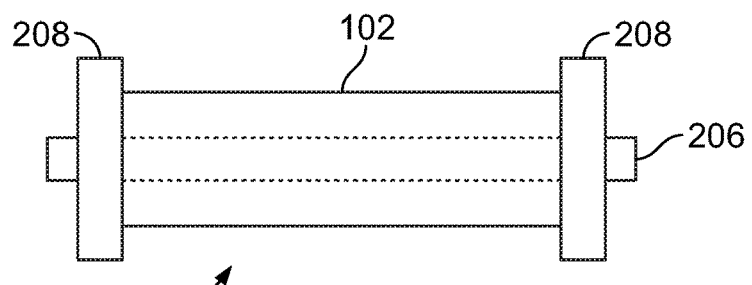
FIG. 4 illustrates a top view of an axle inspection system coupled to an axle, according to an embodiment of the present disclosure.

FIG. 4 illustrates a top view of the axle inspection system 100 coupled to an axle 206, according to an embodiment of the present disclosure. In this embodiment, the axle coupler 102 may fully extend between the wheels 208. The ultrasound scanning assembly 104 (shown in FIG. 1) may also extend fully between the wheels 208. In this embodiment, the axle inspection system 100 may not include the actuator 108, as the axle inspection system 100 covers all or substantially all of the axle 206.

Figure 5:
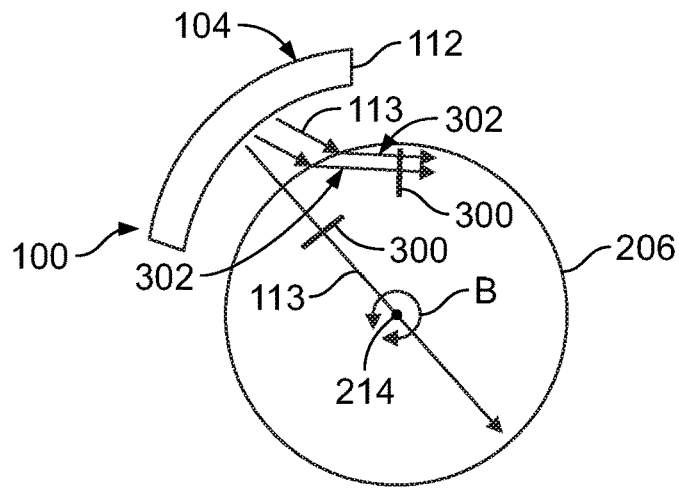
FIG. 5 illustrates a cross-sectional view of an axle inspection system coupled to an axle through line 5-5 of FIG. 3, according to an embodiment of the present disclosure.

FIG. 5 illustrates a cross-sectional view of the axle inspection system 100 coupled to the axle 206 through line 5-5 of FIG. 3, according to an embodiment of the present disclosure. The axle coupler 102, for example, is not shown in FIG. 5. In the illustrated embodiment, the ultrasound scanning assembly 104 includes the first ultrasound probe 112, such a curved transducer array that is configured to transmit ultrasound signals 113 in radial directions with respect to the axle 206. Anomalies 300 may be present within the axle 206. The ultrasound scanning assembly 104 receives reflected signals from the anomalies 300, which are then analyzed by the axle inspection control unit 106, for example.

The axle inspection control unit 106 operates the first ultrasound probe 112 to steer the transmit signals 113 in desired directions 302. The direction 302 may be based on historical data stored within the memory 107 (shown in FIG. 1). The historical data may be or otherwise include information based on typical locations of anomalies within axles.

The frequency of the transmit signals 113 may be determined by the size of the anomalies 300 to be detected. For example, the axle inspection control unit 106 may operate the ultrasound scanning assembly 104 to emit the transmit signals at a wavelength that is twice the width of a typical anomaly based on historical data.

As the axle 206 rotates in the directions of arc B about the longitudinal axis 214, the fixed ultrasound scanning system 104 emits the transmit signals 113 into an entire circumferential area of the axle 206. Accordingly, the relative motion between the axle 206 and the ultrasound scanning assembly 104 ensures that all radial portions of the axle 206 are inspected.

Figure 6:
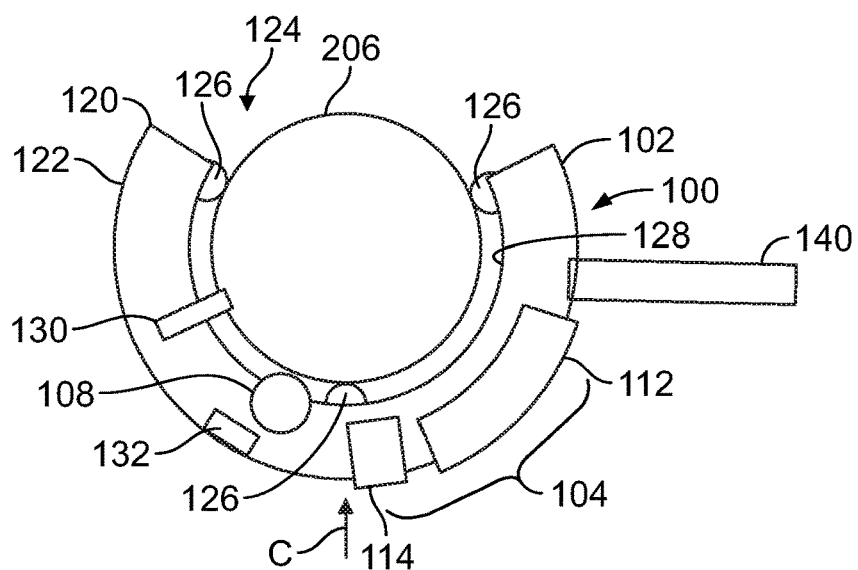
FIG. 6 illustrates a cross-sectional view of an axle inspection system coupled to an axle through line 5-5 of FIG. 3, according to an embodiment of the present disclosure.

FIG. 6 illustrates a cross-sectional view of the axle inspection system 100 coupled to the axle 206 through line 5-5 of FIG. 3, according to another embodiment of the present disclosure. In this embodiment, the axle coupler 102 includes a bracket 120 (such as a yoke or collar) having a main body 122 shaped as a C defining an upper open end 124. Spring-biased rollers 126 inwardly extend from an interior surface 128 of the main body 122. The axle coupler 102 retains the ultrasound scanning system 104 including the first ultrasound probe 112 and the second ultrasound probe 114.

A brush 130 (such as a wire brush) inwardly extends from the interior surface 128 and abuts into an outer surface of the axle 206. As the axle 206 rotates, the brush 130 removes impurities (such as rust, debris, oil, and/or the like) from the axle 206, thereby ensuring that the ultrasound scanning assembly 104 transmits and receives ultrasound signals in relation to a clean surface of the axle 206.

A proximity sensor 132 may also be mounted to the axle coupler 102. The proximity sensor 132 is in communication with the axle inspection control unit 106 (shown in FIG. 1) through one or more wired or wireless connections. The proximity sensor 132 may be an infrared red sensor, ultrasonic sensor, position encoder, switch, and/or the like that is configured to detect a distance to one or both of the wheels 208 (shown in FIGS. 2-4). Based on the position of the axle inspection system 100 in relation to one or both wheels 208, the axle inspection control unit 106 may activate or deactivate the ultrasound scanning assembly 104. For example, as the proximity sensor 132 outputs a proximity signal that indicates that the axle coupler 102 abuts into an interior surface of a wheel, the axle inspection control unit 106 may deactivate the ultrasound scanning assembly 104.

The actuator 108 may be or include a canted wheel, a worm screw, a worm wheel, gears, pulleys, and/or the like that engage an outer surface of the axle 206 and axially move the axle inspection system 100 over a length of the axle 206 in response to rotation of the axle 206. Alternatively or additionally, the actuator 108 may include a motor, for example, that drives motion of the axle inspection system 100 over a length of the axle 206.

In order to secure the axle inspection system 100 to the axle 206, the upper open end 124 is aligned with the axle 206 and urged upwardly onto the axle 206 in the direction of arrow C. As the spring-biased rollers 126 engage the outer surface of the axle 206, the rollers 126 inwardly deflect, while simultaneously exerting a retaining force into the axle 126, thereby ensuring that the axle inspection system 100 remains coupled to the axle 206. Because the axle coupler 102 includes the upper open end 124, the axle inspection system 100 is configured to be easily coupled to the axle from below in the direction of arrow C. Optionally, instead of the rollers 126, the axle coupler 102 may include one or more magnets that securely and removably connect the axle coupler 102 to the axle 206.

A connecting link 140 (such as a beam, arm, bracket, or the like) may connect the axle inspection system 100 to another axle coupler 102. As such, the axle inspection system 100 may include multiple axle couplers 102 supporting multiple ultrasound scanning assemblies 104 that are configured to inspect multiple axles at one time. In such an embodiment, a single axle inspection control unit 106 may be in communication with all of the ultrasound scanning assemblies 104. Optionally, a separate and distinct ultrasound scanning assembly 104 may be used for each separate and distinct axle 206.

Figure 7:
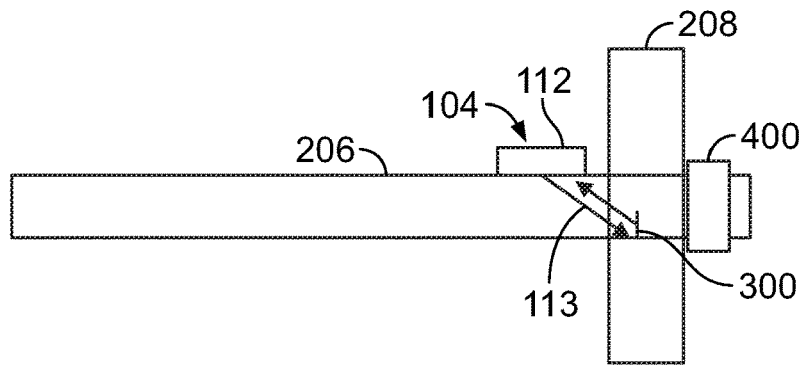
FIG. 7 illustrates a front view of an ultrasound probe in relation to an axle, according to an embodiment of the present disclosure.

FIG. 7 illustrates a front view of the ultrasound probe 114 in relation to the axle 206, according to an embodiment of the present disclosure. As noted above, the ultrasound probe 114 may be a linear ultrasound array that is secured to the axle coupler 102 (not shown in FIG. 7, for clarity). The axle inspection control unit 106 (shown in FIG. 1) may be configured to steer transmitted ultrasound signals 113 axially from the ultrasound probe 114 to portions of the axle within the wheel 208 and/or a bearing 400. In this embodiment, a corner trap is created by the anomaly 300 (such as a crack) that reflects the transmitted signal back to the ultrasound probe 114. As such, the ultrasound probe 114 is configured to transmit and receive ultrasound signals with respect to portions of the axle 206 over which the axle inspection system 100 is blocked from traveling over.

Figure 8:
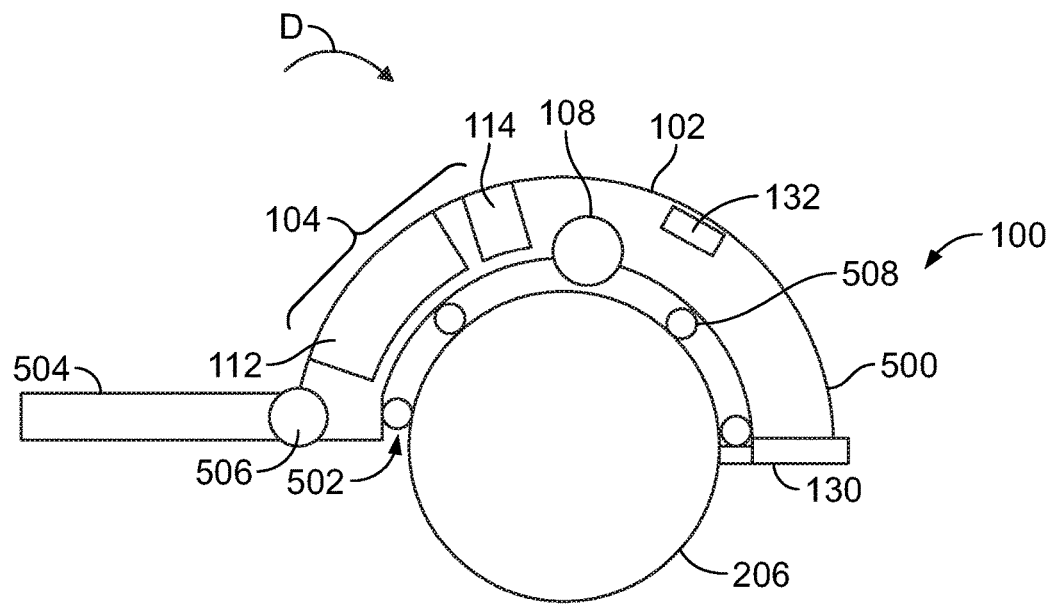
FIG. 8 illustrates a cross-sectional view of an axle inspection system coupled to an axle through line 5-5 of FIG. 3, according to an embodiment of the present disclosure.

FIG. 8 illustrates a cross-sectional view of the axle inspection system 100 coupled to the axle 206 through line 5-5 of FIG. 3, according to yet another embodiment of the present disclosure. The axle inspection system 100 is similar to that shown and described with respect to FIG. 6, except that axle coupler 102 includes a collar 500 having an open lower mouth 502. The collar 500 may be pivotally coupled to a link 504 through a hinge 506. As such, the axle coupler 102 may be pivoted down over the axle 206 in the direction of arc D. Spring-loaded bearings 508 may inwardly extend from the collar 500 and contact an outer surface of the axle 206. The collar 500 remains secured to the axle 206 through gravity, as the collar 500 rests on top of the axle 206.

Figure 9:
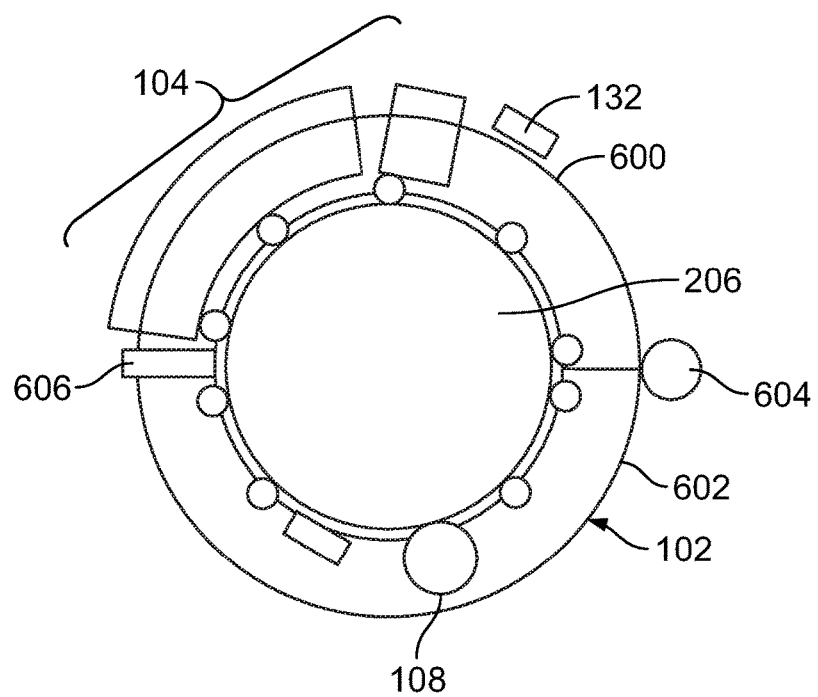
FIG. 9 illustrates a cross-sectional view of an axle inspection system coupled to an axle through line 5-5 of FIG. 3, according to an embodiment of the present disclosure.

FIG. 9 illustrates a cross-sectional view of the axle inspection system 100 coupled to the axle 206 through line 5-5 of FIG. 3, according to still another embodiment of the present disclosure. In this embodiment, the axle coupler 102 includes a top bracket 600 pivotally coupled to a bottom bracket 602 through a hinge 604. The hinge 604 allows the top and bottom brackets 600 and 602 to be pivoted between open and closed positions. A lock 606 may be used to securely lock free ends of the brackets 600 and 602 together to fully close the brackets 600 and 602 around a circumferential portion of the axle 206.

The lock 606 may include a pressure switch coupled to the ultrasound scanning assembly 104. The pressure switch may send an activation signal to the ultrasound scanning assembly 104 when the brackets 600 and 602 are locked around the axle 206. As such, the ultrasound scanning assembly 104 may initiate ultrasonic scanning of the axle 206 in response to the brackets 600 and 602 being locked around the axle 206.

Figure 10:
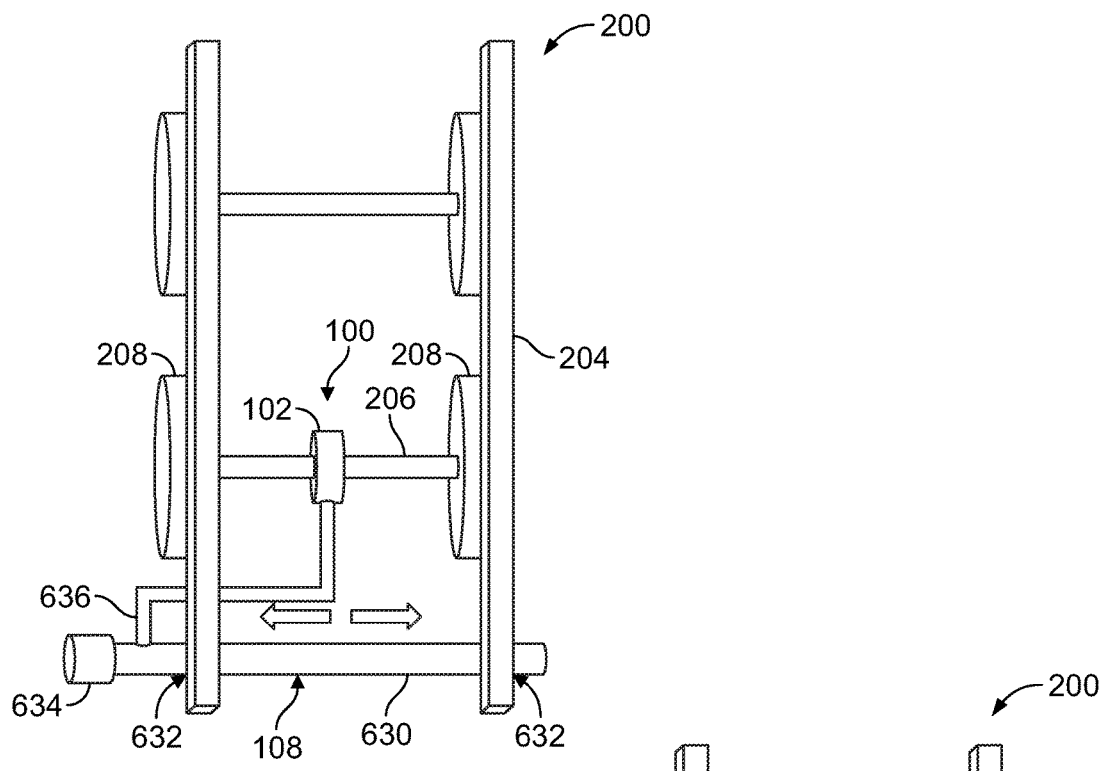
FIG. 10 illustrates a top view of an axle inspection system coupled to an axle of a vehicle, according to an embodiment of the present disclosure.

FIG. 10 illustrates a top view of the axle inspection system 100 coupled to an axle 206 of the vehicle 200, according to an embodiment of the present disclosure. The coupler 102 moveably couples the ultrasound scanning assembly 104 (hidden from view) to the axle 206, such as described with respect to any of the embodiments of the present disclosure.

The actuator 108 may include a beam 630 that is secured to the frame 204 behind (or in front of) the axle 206. For example, the actuator 108 may be removably secured to the frame 204 through magnets 632, fasteners, brackets, and/or the like. The actuator 108 may include a motor 634 (such as a stepper or linear motor) that is operatively coupled to a link 636 that connects to the axle coupler 102. The motor 634 operates to move the link 636 over and/or through the beam 630, thereby moving the axle coupler 102 (and the ultrasound scanning assembly 104) axially over the axle 206.

Figure 11:
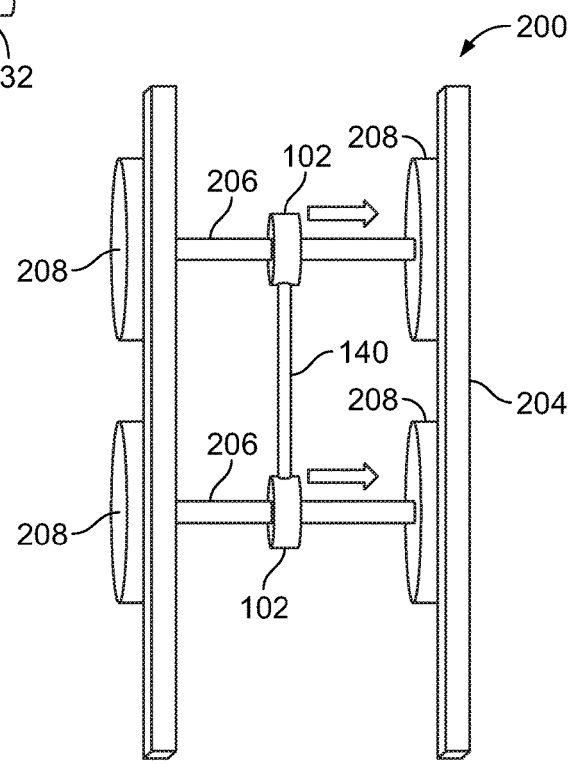
FIG. 11 illustrates a top view of an axle inspection system coupled to axles of a vehicle, according to an embodiment of the present disclosure.

FIG. 11 illustrates a top view of the axle inspection system 100 coupled to axles 206 of the vehicle 200, according to an embodiment of the present disclosure. The axle inspection system 100 may include two axle couplers 102 securely retaining two ultrasound scanning assemblies 104 (hidden from view in FIG. 11) coupled together by the link 140. The link 140 may be sized to separate the axle couplers 102 a distance that corresponds to a standard separation distance between the axles 206 of the vehicle 200 (such as a standard separation distance between two axles of a train car). In this manner, the axle inspection system 100 may be quickly and easily coupled to multiple axles 206 at the same time. In at least one other embodiment, the axle inspection system 100 may link additional axle couplers 102 to the two axle couplers 102, such as through additional links 140.

The axle couplers 102 may axially move over the axles 206 in response to rotation of the axles 206. For example, actuators 108 in the form of worm wheels may engage the axles 206 and move the axle couplers 102 axially in response to the rotational motion of the axles 206.

In at least one embodiment, the axle inspection system 100 may be coupled to the axles 206 manually. In at least one other embodiment, the axle inspection system 100 may be coupled to the axles 206 through a mechanical lift, robotic arm, and/or the like.

As noted, a separate and distinct axle inspection control units 106 may be associated with each of the axle couplers 102. In at least one other embodiment, a single axle inspection control unit 106 may be associated with both of the axle couplers 102.

Figure 17:
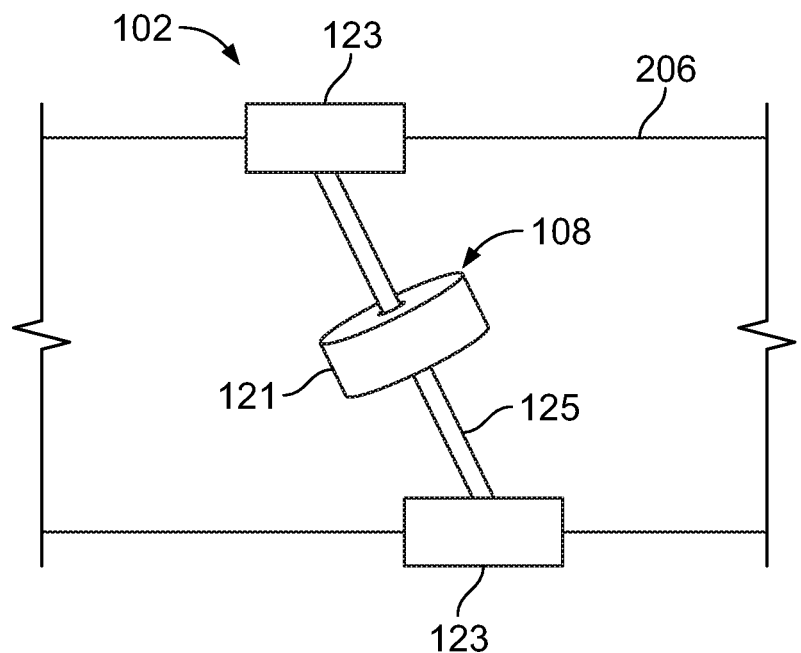
FIG. 17 illustrates a top view of an actuator coupled to an axle, according to an embodiment of the present disclosure.
Figure 18:
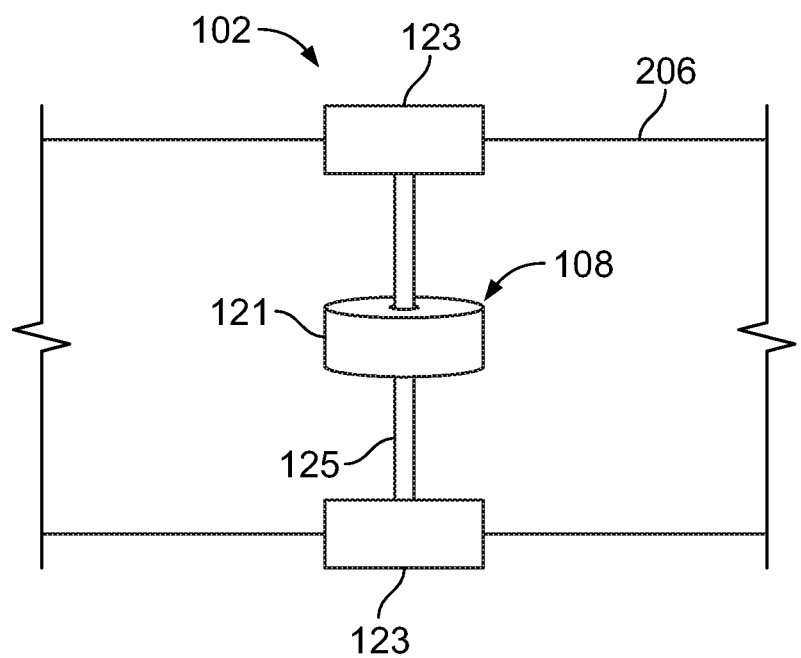
FIG. 18 illustrates a lateral view of an actuator coupled to an axle, according to an embodiment of the present disclosure.

FIG. 17 illustrates a top view of the actuator 108 coupled to the axle 206, according to an embodiment of the present disclosure. FIG. 18 illustrates a lateral view of the actuator 108 coupled to the axle 206. Referring to the embodiment shown in FIGS. 17 and 18, the actuator 108 may include a worm wheel 121 coupled to positioners 123 (such as rollers) by a connecting axle 125. The positioners 123 are coupled to the connecting axle 125 (such as through a rotatable connection). The worm wheel 121 rotates on the connecting axle 125. The positioners 123 are configured to allow for angular and positional adjustment of the worm wheel 121 relative to the axle 206.

In operation, the worm wheel 121 is set at an adjustable angle, and pulls the axle coupler 102 along the axle 206 as the axle 206 rotates. Pressure against the axle 206 may be provided by the positioners 123, such as through a spring-biased relationship with respect to the connecting axle 125, and/or via reaction to a compressive load on wheels (such as rubber wheels) of the positioners 123.

Figure 12:
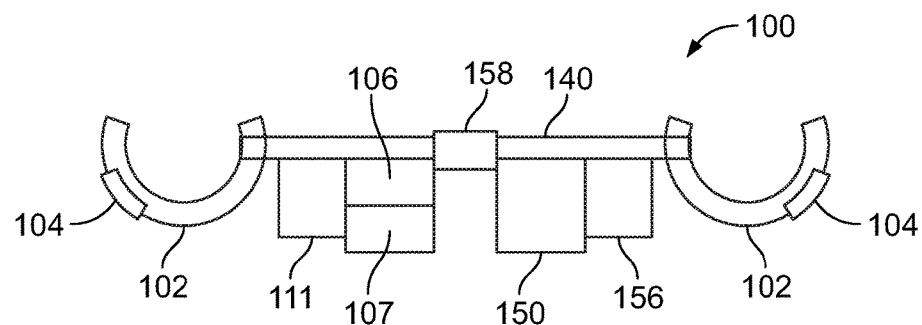
FIG. 12 illustrates a lateral view of an axle inspection system, according to an embodiment of the present disclosure.

FIG. 12 illustrates a lateral view of the axle inspection system 100, according to an embodiment of the present disclosure. As shown, two axle couplers 102 carry respective ultrasound scanning assemblies 104. A pulse generator and receiver 156 may be connected to the ultrasound scanning assemblies 104, and in communication with the axle inspection control unit 106. Optionally, the ultrasound scanning assemblies 104 may include the pulse generator and receiver 156. A power supply 150 may be coupled to the axle inspection control unit 106, the memory 107, the pulse generator and receiver 156, and the ultrasound scanning assemblies 104. The power supply 150 may be a battery, for example.

The link 140 may include a central beam 158. The beam 158 may provide a lift point that is configured to be engaged by an installation device (such as a robotic arm, mechanical lift, or the like). For example, the installation device may support and hold the axle inspection system 100 at the central beam 158.

Figure 13:
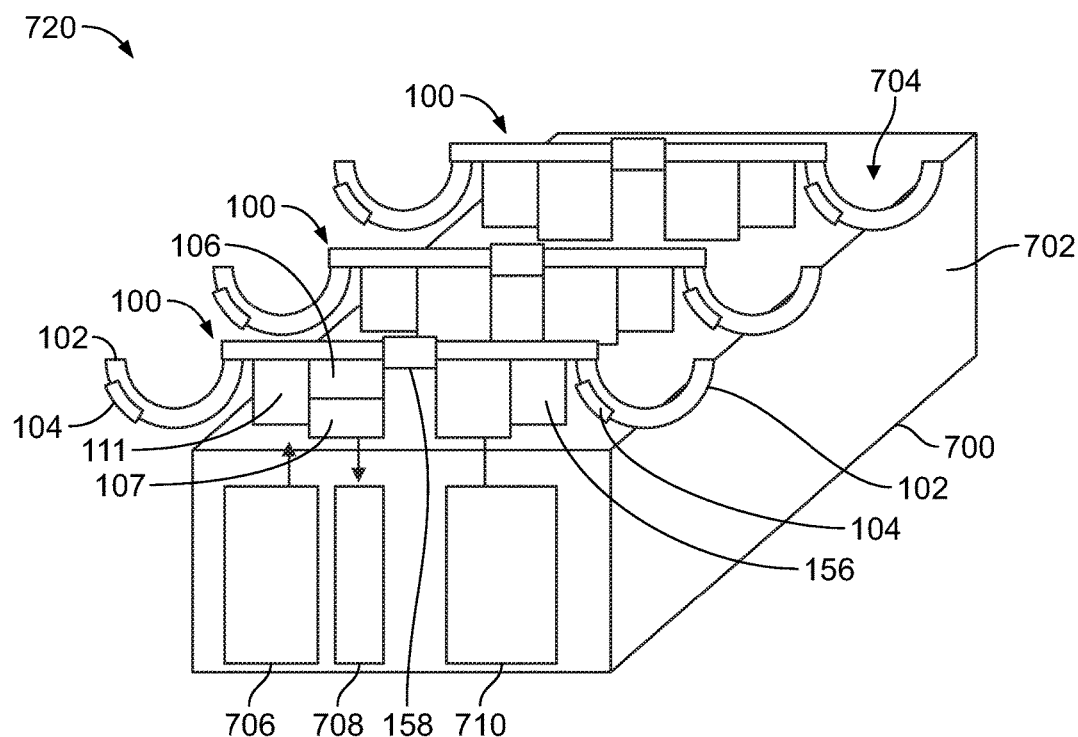
FIG. 13 illustrates a simplified perspective top view of axle inspection systems coupled to a staging system, according to an embodiment of the present disclosure.

FIG. 13 illustrates a simplified perspective top view of axle inspection systems 100 coupled to a staging system 700, according to an embodiment of the present disclosure. The staging system 700 includes a housing having an internal chamber 704 that retains a couplant reservoir 706, a data storage unit 708, and a power recharger 710. The individual axle inspection system 100 may be stored on and/or within the staging system 700 and coupled to the couplant reservoir 706 (to replenish couplant), the data storage unit 708 (to download anomaly data to and/or upload data from the data storage unit 708), and the power recharger 710 to recharge the power supplies 150. An installation device (not shown in FIG. 13) may lift and remove the axle inspection systems 100 from the staging system 700 via the central beams 158 and install them on axles of a vehicle. The installation device (or a separate removal device) may remove the axle inspection systems 100 from the axles and return the axle inspection systems 100 to the staging system 700.

A vehicle examination system 720 includes the axle inspection system 100 and the staging system 700. The vehicle examination system 720 is configured to be used to examine one or more vehicles, such as the axles of the vehicles.

Figure 14:
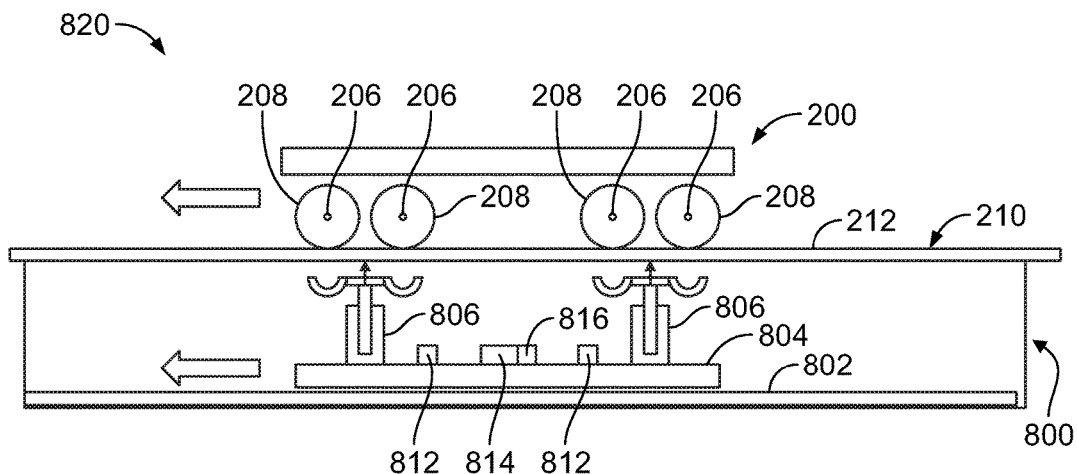
FIG. 14 illustrates a lateral view of an installation system that is configured to install axle inspection systems onto axles of a vehicle, according to an embodiment of the present disclosure.

FIG. 14 illustrates a lateral view of an installation system 800 that is configured to install axle inspection systems 100 onto axles of a vehicle, according to an embodiment of the present disclosure. The installation system 800 may include a base track 802 supporting an installation cart 804 moveably coupled to the base track 800. The installation system 800 may be underneath the tracks 212 onto which the vehicle 200 is moveably supported. The installation cart 804 includes one or more installation devices 806, such as robotic arms, pneumatic or hydraulic cylinders, and/or the like that are configured to position the axle inspection systems 100 onto the axles 206, as described above. The installation cart 804 may move along with the vehicle to securely connect the axle inspection systems 100 as the vehicle 200 is moving on the tracks 212.

The installation cart 804 may also include one or more imaging devices 812 (such as digital cameras) that are configured to image the axles 206 before the axle inspection systems 100 are coupled thereto. Optionally, the imaging devices 812 may be separate and distinct from the installation cart 804. The captured images may be analyzed by the axle inspection control unit 106 (shown in FIG. 1, for example) and/or a control unit 814 of the installation system 800 to determine whether or not the axle inspection systems 100 are to be coupled to the axles 206. For example, certain axles 206 may include components thereon that prevent the axle inspection systems 100 from being coupled thereto. Other axles 206 may be incompatible with the axle inspection systems 100. One or more of the control units 106 and/or 814 compare the captured images of the axles 206 with axle compatibility data stored in the memories 107 (shown in FIG. 1) and/or a memory 816 of the installation system 800 to determine whether or not to couple the axle inspection systems 100 to the axles 206.

After the axle inspection processes are complete, the installation devices 806 (or separate removal devices) remove the axle inspection systems 100 from the axles 206. The installation devices 806 may then return to the axle inspection systems 100 to the staging system 700 (shown in FIG. 13).

A vehicle examination system 820 includes the axle inspection systems 100 and the installation system 800 (and/or the staging system 700 shown in FIG. 13). The vehicle examination system 820 is configured to be used to examine one or more vehicles, such as the axles 206 of the vehicle 200.

Figure 15:
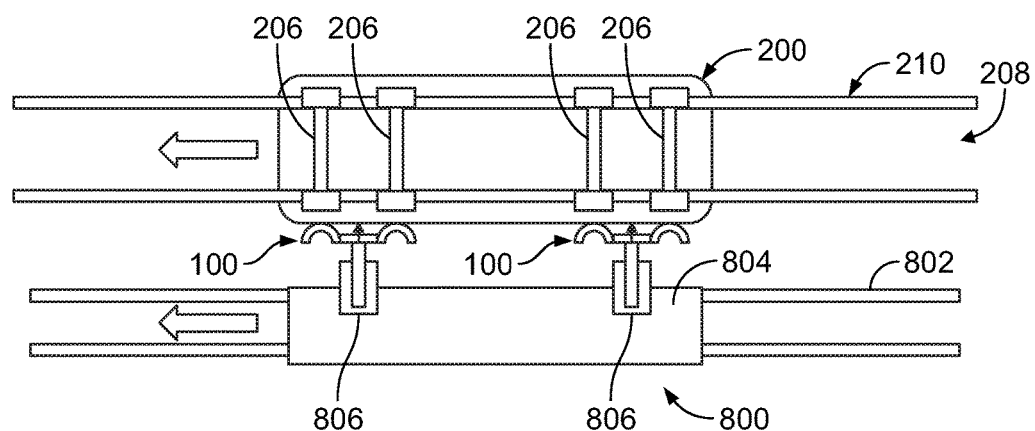
FIG. 15 illustrates a top view of an installation system that is configured to install axle inspection systems onto axles of a vehicle, according to an embodiment of the present disclosure.

FIG. 15 illustrates a top view of the installation system 800 that is configured to install axle inspection systems 100 onto the axles 206 of the vehicle 200, according to an embodiment of the present disclosure. The installation system 800 is similar to that described with respect to FIG. 14, except that the installation system 800 is positioned to a side of the vehicle 200, and is configured to install the axle inspection systems 100 laterally onto the axles 206, instead of from below.

Figure 16:
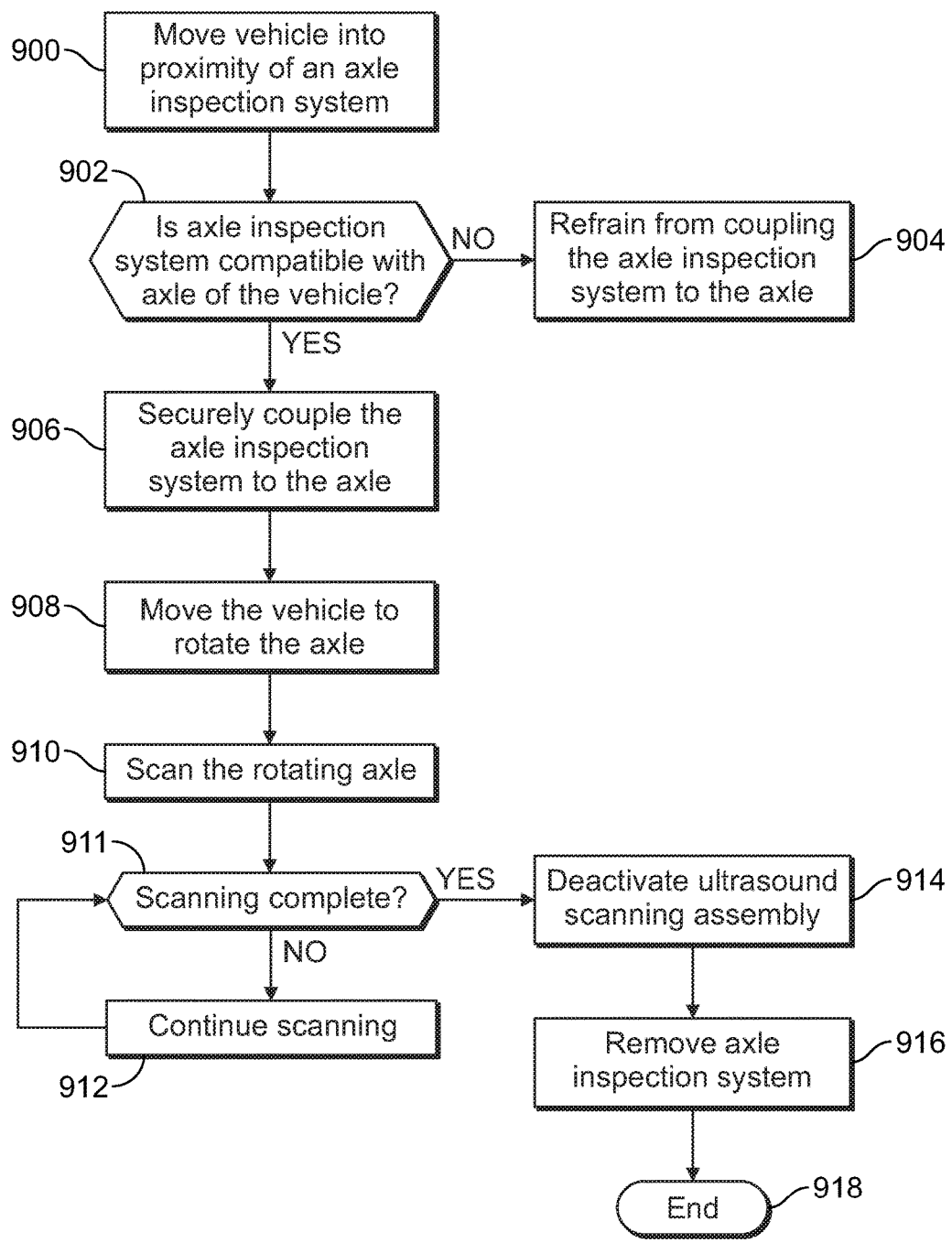
FIG. 16 illustrates a flow chart of a method of inspecting an axle of a vehicle, according to an embodiment of the present disclosure.

FIG. 16 illustrates a flow chart of a method of inspecting an axle of a vehicle, according to an embodiment of the present disclosure. The method begins at 900, in which a vehicle is moved in proximity to an axle inspection system. At 902, it is determined whether the axle inspection system is compatible with the axle of the vehicle. For example, an individual may view the axle and determine whether or not the axle inspection system and the axle are compatible. In at least one other embodiment, a control unit (such as the control unit 814 shown in FIG. 14, or the axle inspection control unit shown in FIG. 1) may compare captured image data with stored compatibility data to determine compatibility. If the axle inspection system is not compatible with the axle, the method proceeds from 902 to 904, in which the axle inspection system is not coupled to the axle.

If, however, the axle inspection system is compatible with the axle at 902, the method proceeds from 902 to 906, in which the axle inspection system is securely coupled to the axle. The axle inspection system may be manually coupled to the axle, or may be automatically coupled to the axle through an installation device, such as shown and described with respect to FIGS. 14 and 15.

At 908, the vehicle is moved to rotate the axle. The rotating axle is scanned by an ultrasound scanning assembly of the axle inspection system at 910. At 911, it is determined whether the scanning is complete. For example, the axle inspection control unit 106 of FIG. 1 determines if an entire desired portion of the axle has been scanned. If the scanning is not complete, the method proceeds from 911 to 912, in which the scanning continues. The method then returns to 911.

If, however, the scanning is complete at 911, the method proceeds from 911 to 914, in which the ultrasound scanning assembly is deactivated (such as by the axle inspection control unit 106). Then at 916, the axle inspection system is removed from the axle, either manually or through an installation or removal device. At 918, the method ends.

Referring to FIGS. 1-16, embodiments of the present disclosure provide axle inspection systems and methods that provide efficient inspection of axles of a vehicle. The systems and methods may automatically inspect axles of vehicles. Unlike prior systems, embodiments of the present disclosure provide axle inspection systems and methods that inspect axles of a vehicle for anomalies as the vehicle moves.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A vehicle examination system comprising:
    an axle inspection system that is configured to inspect an axle of a vehicle, wherein the axle inspection system comprises:
        an ultrasound scanning assembly;
        an axle coupler that retains the ultrasound scanning assembly, wherein the axle coupler is configured to moveably secure the ultrasound scanning assembly to the axle; and
        an axle inspection control unit in communication with the ultrasound scanning assembly, wherein the axle inspection control unit is configured to control the ultrasound scanning assembly to ultrasonically scan the axle for anomalies as the vehicle moves.

2. The vehicle examination system of claim 1, wherein the axle coupler axially moves over the axle as the axle rotates.

3. The vehicle examination system of claim 1, wherein the axle coupler is configured to be coupled to the axle as the vehicle is moving.

4. The vehicle examination system of claim 1, wherein the axle inspection system further comprises a memory coupled to the axle inspection control unit, wherein the memory stores historical data regarding anomalies in axles, and wherein the axle inspection control unit controls the ultrasound scanning assembly to transmit ultrasound signals into areas of the axle based on the historical data.

5. The vehicle examination system of claim 1, wherein the axle inspection system further comprises an actuator that propels the axle coupler over the axle.

6. The vehicle examination system of claim 5, wherein rotation of the axle causes the actuator to propel the axle coupler over the axle.

7. The vehicle examination system of claim 5, wherein the actuator comprises a motor that propels the axle coupler over the axle.

8. The vehicle examination system of claim 1, wherein the ultrasound scanning assembly comprises at least ultrasound probe.

9. The vehicle examination system of claim 8, wherein the at least one ultrasound probe is configured to radially scan the axle.

10. The vehicle examination system of claim 8, wherein the at least one ultrasound probe is configured to axially scan the axle.

11. The vehicle examination system of claim 1, wherein the axle coupler comprises at least one C-shaped bracket that is configured to directly engage the axle, wherein the at least one C-shaped bracket comprises a plurality of spring-biased rollers that are configured to engage an outer surface of the bracket.

12. The vehicle examination system of claim 1, further comprising a staging system including an internal chamber that houses a couplant reservoir, a data storage unit, and a power recharger, wherein the axle inspection system is configured to be moved between the staging system and the axle.

13. The vehicle examination system of claim 1, further comprising an installation system comprising an installation cart that is configured to move along with the vehicle and install the axle inspection system on the axle of the vehicle as the vehicle and the installation cart move, wherein the installation cart comprises an installation device that is configured to automatically install the axle inspection system onto the axle.

14. A vehicle examination method comprising:
    inspecting an axle of a vehicle with an axle inspection system, wherein the inspecting comprises:
        retaining an ultrasound scanning assembly with an axle coupler;
        moveably securing the ultrasound scanning assembly to the axle with the axle coupler;
        communicatively coupling an axle inspection control unit to the ultrasound scanning assembly;
        moving the vehicle; and
        controlling the ultrasound scanning assembly with the axle inspection control unit to ultrasonically scan the axle for anomalies during the moving.

15. The vehicle examination method of claim 14, wherein the moveably securing comprises coupling the axle coupler to the axle as the vehicle is moving.

16. The vehicle examination method of claim 14, further comprising storing historical data regarding anomalies in axles in a memory, wherein the controlling comprises transmitting ultrasound signals into areas of the axle based on the historical data.

17. The vehicle examination method of claim 14, further comprising propelling the axle coupler over the axle with an actuator.

18. The vehicle examination method of claim 17, wherein the propelling comprises rotating the axle to cause the actuator to propel the axle coupler over the axle.

19. The vehicle examination method of claim 14, wherein the controlling comprises radially scanning the axle with the ultrasound scanning assembly.

20. The vehicle examination method of claim 14, further comprising moving the axle inspection system between a staging system and the axle.

21. The vehicle examination method of claim 14, wherein the axle coupler comprises at least one C-shaped bracket that is configured to directly engage the axle, wherein the at least one C-shaped bracket comprises a plurality of spring-biased rollers that are configured to engage an outer surface of the bracket.

22. The vehicle examination method of claim 20, wherein the staging system includes an internal chamber that houses a couplant reservoir, a data storage unit, and a power recharger.

23. The vehicle examination method of claim 14, further comprising:
- moving an installation system including an installation cart along with the vehicle; and
- installing the axle inspection system on the axle of the vehicle as the vehicle and the installation cart move, wherein the installing comprises using an installation device of the installation cart to automatically install the axle inspection system onto the axle.

\* \* \* \* \*